(12) United States Patent  (10) Patent No.: US 8,535,651 B2
Chen et al.  (45) Date of Patent: Sep. 17, 2013

(54) WATER SOLUBLE POLYMER COMPLEXES WITH SURFACTANTS

(75) Inventors: Shih-Ruey T Chen, Pittsburgh, PA (US); Kevin W. Frederick, Evans City, PA (US)

(73) Assignee: WSP Chemicals & Technology, LLC, Ambridge, PA (US)

( * ) Notice: Subject to any disclaimer, the term of this patent is extended or adjusted under 35 U.S.C. 154(b) by 0 days.

(21) Appl. No.: 13/493,092

(22) Filed: Jun. 11, 2012

(65) Prior Publication Data

US 2012/0251475 A1   Oct. 4, 2012

Related U.S. Application Data

(62) Division of application No. 11/108,352, filed on Apr. 18, 2005, now Pat. No. 8,211,414.

(60) Provisional application No. 60/563,429, filed on Apr. 19, 2004.

(51) Int. Cl.
  *A61K 8/81* (2006.01)

(52) U.S. Cl.
  USPC ........................ 424/70.16; 424/401

(58) Field of Classification Search
  None
  See application file for complete search history.

(56) References Cited

U.S. PATENT DOCUMENTS

| | | | |
|---|---|---|---|
| 2,438,091 A | 3/1948 | Lynch | |
| 2,528,378 A | 10/1950 | Mannheimer et al. | |
| 2,658,072 A | 11/1953 | Milton et al. | |
| 3,986,825 A | 10/1976 | Sokol | |
| 4,152,416 A | 5/1979 | Spitzer et al. | |
| 4,175,572 A | 11/1979 | Hsiung et al. | |
| 4,578,267 A | 3/1986 | Salamone | |
| 4,803,071 A | 2/1989 | Iovine et al. | |
| 4,859,458 A | 8/1989 | Salamone et al. | |
| 4,874,604 A | 10/1989 | Sramek | |
| 4,923,694 A | 5/1990 | Shih et al. | |
| 5,089,252 A | 2/1992 | Grollier et al. | |
| 5,275,809 A | 1/1994 | Chen et al. | |
| 5,296,218 A | 3/1994 | Chen et al. | |
| 5,609,862 A | 3/1997 | Chen et al. | |
| 5,879,670 A | 3/1999 | Melby et al. | |
| 6,066,315 A | 5/2000 | Melby et al. | |
| 6,566,313 B1 | 5/2003 | Hohenstein et al. | |
| 6,663,855 B2 | 12/2003 | Frechet et al. | |
| 7,074,244 B2 | 7/2006 | Chan et al. | |
| 2003/0064044 A1 | 4/2003 | Chen et al. | |

FOREIGN PATENT DOCUMENTS

| | | |
|---|---|---|
| EP | 0 308 189 | 3/1989 |
| EP | 0 308 190 | 3/1989 |

*Primary Examiner* — Bethany Barham
(74) *Attorney, Agent, or Firm* — Blynn L. Shideler; Krisanne Shideler; BLK Law Group

(57) ABSTRACT

A complex including a polymer and a surfactant formed by polymerizing a monomer mixture containing:
  (A) acid functional monomers at least partially neutralized with one or more amines according to one or more of formulas (I) through (IV):

$$R^1-NR^2R^3 \qquad (I)$$

$$R^1-N^+R^2R^3R^7X^- \qquad (II)$$

$$R^4-C(O)-NR^5-R^6-NR^2R^3 \qquad (III)$$

$$R^4-C(O)-NR^5-R^6-N^+R^2R^3R^7X^- \qquad (IV)$$

wherein $R^1$ and $R^4$ are independently a $C_8$-$C_{24}$ group; $R^2$, $R^3$ and $R^5$ are independently H or a $C_1$-$C_6$ group, or where $R^2$ and $R^3$ combine to form an anelled ring of from 4 to 12 carbon atoms in length optionally containing hetero atoms; $R^6$ is $C_1$-$C_{24}$ group, $R^7$ is H or a $C_1$-$C_{12}$ group, and X is a halide, a sulfate or a sulfonate;
  (B) one or more cationic monomers; and optionally
  (C) one or more other monomers.

17 Claims, No Drawings

WATER SOLUBLE POLYMER COMPLEXES WITH SURFACTANTS

CROSS-REFERENCE TO RELATED APPLICATIONS

This application is a Division of Application. Ser. No. 11/108,352, now U.S. Pat. No. 8,211,414, filed Apr. 18, 2005 and entitled "Water-Soluble Polymer Complexes with Surfactants," which claims the benefit of U.S. Provisional Patent Application Ser. No. 60/563,429, filed Apr. 19, 2004, and entitled "Water-soluble Polymer Complexes with Surfactants."

BACKGROUND OF THE INVENTION

1. Field of the Invention

The present invention relates to polymer-surfactant compositions and methods for using such compositions, and formulations containing them in personal care applications. The formulations can be hair or skin care products such as conditioners, hair dyes, permanent waves, hair relaxers, hair bleaches, hair setting compositions, styling gels, mousses, hair gels, aftershaves, sunscreens, hand lotions, moisturizers and shaving creams.

2. Brief Description of the Prior Art

The surface properties of keratin are of interest in cosmetic science, and there has been a long-standing desire to discover ingredients which will beneficially affect the topical and bulk condition of keratinous substrates, such as hair and skin. For example, such ingredients must have adequate adherent properties, so that they are not only adsorbed initially, but are also retained on exposure to water. This property is referred to as "substantivity," i.e., the ability of a material to be adsorbed onto keratin and to resist removal by water rinse-off.

Hair is composed of keratin, a sulfur-containing fibrous protein. The iso-electric point of keratin, and more specifically of hair, is generally in the pH range of 3.2 to 4.0. Therefore, at the pH of a typical shampoo, hair carries a net negative charge. Consequently, cationic polymers have long been used as conditioners in shampoo formulations, or as a separate treatment, in order to improve the wet and dry combability of the hair. The substantivity of the cationic polymers for negatively charged hair along with film formation facilitates detangling during wet hair combing and reducing static flyaway during dry hair combing. Cationic polymers generally also impart softness and suppleness to hair.

When cationic polymers are added to shampoos (or to skin care products such as cleaning compositions) containing anionic surfactants, formation of highly surface active association complexes generally takes place, which imparts improved foam stability to the shampoo. Maximum surface activity and foam stability, or lather, are achieved at near stoichiometric ratios of anionic surfactant to cationic polymer, where the complex is least water soluble. Generally, cationic conditioners exhibit some incompatibility at these ratios. Compatibility gives a commercially more desirable clear formulation, while incompatibility leads to a haze or precipitation, which is aesthetically less desirable in some formulations.

Hair fixative properties such as curl retention are believed to be directly related to film-forming properties of cationic polymers as well as to molecular weight, with performance generally increasing with increasing molecular weight. However, the fixative properties conferred by cationic polymers generally tend to have a reciprocal relationship to other conditioning properties, i.e., good curl retention usually means that properties such as wet combability will suffer, and vice versa.

Keratin conditioning additives generally are of three primary types: cationic polymers, proteins or protein derivatives and fatty quaternary ammonium compounds. Commonly used cationic polymers include quaternary nitrogen-containing hydroxyethyl cellulose compounds, copolymers of vinylpyrrolidone and dimethylamino-ethylmethacrylate, and amino functional polydimethyl-siloxane. Hydrolyzed animal protein has been frequently used as a keratin conditioner. Also used are natural products such as collagen and casein. Suitable quaternary ammonium compounds include such products as stearyl dimethyl ammonium chloride.

Generally, two broad areas of skin care products have been recognized as skin conditioners: emollients and humectants. Emollients generally provide improved moisture retention in the skin and plasticization/softening of the skin. Common commercial emollients are mineral oil; petrolatum; aliphatic alcohols, such as stearyl alcohol; lanolin and its derivatives; glycol stearate; and fatty acids, such as triethanolamine oleate. Humectants generally attract moisture, retard evaporation of water from the skin surface, and plasticize/soften the skin. Common commercial humectants include glycerin, propylene glycol, sorbitols and polyethylene glycols.

A desirable skin conditioner should impart at least some of the attributes of an emollient or a humectant, as well as provide improved lubricity and feel to the skin after treatment and/or reduce skin irritation caused by other components in the conditioner such as, for example, soaps, detergents, foam boosters, surfactants and perfumes. It is known by those skilled in the art that cationic polymers can be employed as skin and nail conditioners.

At times, it is also desirable that the ingredients of skin and nail care products have adequate adherent properties, so that they are not only adsorbed initially, but are also retained on exposure to water. This property, as in hair care applications, is referred to as "substantivity," i.e., the ability of a material contacted with the keratin of skin or nails to resist removal by water rinse-off. Generally, the pH of the keratin under typical use conditions, i.e., on skin and nails, carry a net negative charge. Consequently, cationic polymers have long been used as conditioners in nail and skin care formulations. The substantivity of the cationic polymers for negatively charged skin and nails leads to film formation that facilitates lubricity, moisturizing and feel.

The skin and nail conditioning properties of lubricity, moisturizing and feel are related to the film-forming properties of the cationic polymers, as well as to molecular weight, with performance generally increasing with increasing molecular weight.

Conditioning additives comprising copolymers of dimethyldiallylammonium chloride and other monomers are well known; see, e.g., EP 308189 (with acrylamide), EP 0 308 190 and U.S. Pat. No. 4,803,071 (with hydroxyethyl cellulose). Amphoteric betaines have also been employed in cosmetic compositions; see GB 2,113,245, which discloses use of betainized dialkylaminoalkyl(meth)acrylate together with a cationic polymer.

The use of polymers of dimethyldiallylammonium chloride (DMDAAC) in the treatment of keratin is also known. See, e.g., U.S. Pat. Nos. 4,175,572 and 3,986,825. U.S. Pat. No. 5,296,218 discloses DMDAAC-based ampholyte terpolymers containing acrylamide for hair care applications, while U.S. Pat. No. 5,275,809 discloses DMDAAC-based ampholyte terpolymers containing acrylamidomethylpropane sulfonic acid for hair care uses.

U.S. Pat. No. 4,923,694 to Shih et al. discloses copolymers of vinyl pyrrolidone and (meth)acrylic cationic monomers that are useful for treating hair. These polymers are able to provide good hair styling properties at low concentrations of cationic monomer, but provide limited substantivity due to their relatively low cationic charge density. When the cationic charge density is increased, the polymers disclosed by Shih et al. become difficult to formulate with due to their decreasing compatibility with anionic surfactants.

U.S. Pat. No. 5,609,862 to Chen et al. discloses hair conditioning polymers comprised of acrylamide, acrylic acid and a cationic monomer. The conditioning polymers disclosed by Chen et al. are very compatible with anionic surfactants, but demonstrate poor compatibility with amphoteric and cationic surfactants. Further, the conditioning polymers of Chen et al. provide poor hair styling properties and only minor conditioning benefit to hair.

U.S. Pat. Nos. 5,879,670 and 6,066,315 to Melby et al. disclose conditioning polymers that include acrylic acid or acrylamidomethylpropane sulfonic acid monomers, (meth) acrylamidopropyl trimethyl ammonium chloride cationic monomers and (meth)acrylate ester nonionic monomers. The conditioning polymers of Melby et al. are difficult to formulate at low pH and do not provide good hair styling properties.

U.S. Pat. No. 4,578,267 to Salamone discloses a method of conditioning skin by applying to skin a composition which includes emollients and humectants and a sulfonic acid functional homopolymer neutralized with an alkoxylated nitrogen compound. U.S. Pat. No. 4,859,458 to Salamone et al. discloses similar compositions for use in hair conditioning. The polymers disclosed by Salamone, however, have poor substantivity to keratin substrates.

U.S. Patent Application Publication 2003/0064044 to Chen et al. discloses a composition for treating a keratin-based substrate that includes a cosmetically acceptable medium containing a water-soluble interjacent complex of a first water-soluble polymer and a second water-soluble polymer formed by polymerizing one or more water-soluble monomers in the presence of the first water-soluble polymer.

There remains a need for a polymeric conditioning additive for keratin-based substrates that provides excellent hair styling properties, as well as excellent conditioning properties to hair, skin and nails.

SUMMARY OF THE INVENTION

The present invention is directed to a complex including a polymer and a surfactant formed by polymerizing a monomer mixture containing:

(A) acid functional monomers at least partially neutralized with one or more amines according to one or more of formulas (I) through (IV):

$$R^1\text{—}NR^2R^3 \tag{I}$$

$$R^1\text{—}N^+R^2R^3R^7X^- \tag{II}$$

$$R^4\text{—}C(O)\text{—}NR^5\text{—}R^6\text{—}NR^2R^3 \tag{III}$$

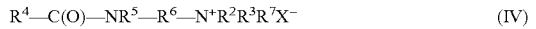

$$R^4\text{—}C(O)\text{—}NR^5\text{—}R^6\text{—}N^+R^2R^3R^7X^- \tag{IV}$$

where $R^1$ and $R^4$ are independently $C_8$-$C_{24}$ linear, branched or cyclic alkyl, aryl, alkenyl, aralkyl or aralkyl; $R^2$, $R^3$ and $R^5$ are independently H or $C_1$-$C_6$ linear, branched or cyclic alkyl; $R^6$ is $C_1$-$C_{24}$ linear, branched or cyclic alkylene, arylene, alkenylene, aralkylene or aralkylene, $R^7$ is H, $C_1$-$C_{12}$ linear, branched or cyclic alkylene, arylene, alkenylene, aralkylene or aralkylene, and X is a halide, a sulfate or a sulfonate;

(B) one or more cationic monomers; and optionally
(C) one or more other monomers.

The present invention is also directed to a composition for treating a keratin-based substrate containing a cosmetically acceptable medium that includes the above-described polymer-surfactant complex.

The present invention also relates to a method of treating a keratin-based substrate including applying a cosmetically acceptable medium containing from 0.1-99.9% by weight of the above-described polymer-surfactant complex to the substrate.

DETAILED DESCRIPTION OF THE INVENTION

Other than in the operating examples, or where otherwise indicated, all numbers or expressions referring to quantities of ingredients, reaction conditions, etc., used in the specification and claims are to be understood as modified in all instances by the term "about."

The terms (meth)acrylic and (meth)acrylate are meant to include both acrylic and methacrylic acid derivatives, such as the corresponding alkyl esters often referred to as acrylates and (meth)acrylates, which the term (meth)acrylate is meant to encompass.

As used herein, the term "keratin" refers to human or animal hair, skin and/or nails.

As used herein, the term "active basis" refers to a concentration of additive based on the active solids in the stock solution.

As used herein, the term "effective amount" refers to that amount of a composition necessary to bring about a desired result, such as, for example, the amount needed to treat a keratin-containing substrate relative to a particular purpose, such as conditioning.

Unless otherwise indicated, all molecular weight values recited herein and in the claims refer to weight average molecular weight (Mw) values determined using gel permeation chromatography (GPC) using appropriate standards.

The present invention is directed to novel water-soluble polymer surfactant complexes and to the use of the same in the treatment of keratin-containing substrates, particularly human skin, hair or nails.

The present water-soluble polymer-surfactant complexes are generally useful in cosmetic formulations and provide particularly improved conditioning and hair styling properties to hair and skin care products. For example, in addition to improved conditioning properties, as measured by combability, substantivity, flyaway and/or hair feel, the present water-soluble polymer surfactant complexes can, at the same time, improve hair fixative properties, such as curl retention and provide moisturizing properties.

In skin and nail conditioning products, the water-soluble polymer surfactant complexes of the present invention function to improve properties such as retention of moisture, softening of the skin, attraction of air moisture, retardation of water loss, feel and reduction of skin irritations caused by contact with cosmetic ingredients.

In particular, the present invention is directed to a complex containing a polymer and a surfactant formed by polymerizing a monomer mixture containing (A) acid functional monomers, (B) one or more cationic monomers and, optionally, (C) one or more other monomers. The acid functional monomers (A) are at least partially neutralized with one or more amines according to one or more of formulas (I) through (IV):

$$R^1\text{—}NR^2R^3 \tag{I}$$

$$R^1\text{—}N^+R^2R^3R^7X^- \tag{II}$$

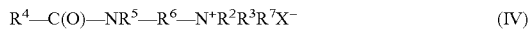

In the present invention, $R^1$ and $R^4$ are independently linear, branched or cyclic alkyl, aryl, alkenyl, aralkyl or aralkyl groups having at least 8 carbon atoms, in some cases at least 10 carbon atoms, in other cases at least 12 carbon atoms and in other cases at least 14 carbon atoms and up to 24 carbon atoms, in some cases up to 20 carbon atoms, and in other cases up to 18 carbon atoms. The number of carbon atoms in $R^1$ and $R^4$ can range between any of the values recited above. In a particular embodiment of the invention, $R^1$ and $R^4$ can be any of the common and/or naturally occurring groups selected from coco, oleyl, ricinoleyl, stearyl, isostearyl, behenyl, lauryl, soyyl, sunfloweryl and mixtures thereof. In many instances, the carbon chain length of $R^1$ and $R^4$ will be a mixture of chain lengths. In a particular embodiment of the invention, at least 75%, in some cases at least 80%, in other cases at least 85%, in some instances at least 90% and up to 100%, in some cases up to 99% and in other cases up to 95% by weight of the $R^1$ and $R^4$ groups will be from $C_8$-$C_{24}$ in length. $R^2$, $R^3$ and $R^5$ can independently be H or $C_1$-$C_6$ linear, branched or cyclic alkyl. In an embodiment of the invention, $R^2$ and $R^3$ can combine to form an anelled ring of from 4 to 12 carbon atoms in length that can optionally contain hetero atoms along the ring selected from O, S, and N and can be cycloalkyl or aromatic in character. A non-limiting example of such a ring is a morpholinyl ring. $R^6$ can be $C_1$-$C_{24}$ linear, branched or cyclic alkylenyl, arylenyl, alkenylenyl, aralkylenyl or aralkylenyl. In a particular embodiment of the invention, $R^6$ is selected from ethylenyl, propylenyl, isopropylenyl, butylenyl and isobutylenyl. $R^7$ can be H or $C_1$-$C_{12}$ linear, branched or cyclic alkylene, arylene, alkenylene, aralkylene or aralkylene. In an embodiment of the invention, $R^7$ is selected from H, methyl, ethyl, propyl, isopropyl, butyl and isobutyl. X is any suitable counter ion and can be a halide, a sulfate or a sulfonate.

In an embodiment of the invention, the amines have an amine value of at least 130, in some cases at least 135, in other cases at least 140 and in some instances at least 150 mg KOH/g. Also, the amines can have an amine value up to 250, in some cases up to 240, and in other cases up to 225 mg KOH/g. The amine value of the amines can vary between any of the values recited above.

The monomer mixture can include anionic monomer (A) at a level of at least 10%, in some cases at least 20%, in other cases at least 25% and in some situations at least 30% based on the number of moles of (A), (B) and (C). When the amount of monomer (A) is too low, the resulting polymer can have poor compatibility and/or not be capable of carrying sufficient surfactant counter ion to provide desired properties. Also, anionic monomer (A) can be present at up to 90%, in some cases up to 80%, in other cases up to 70%, in some situations up to 60% and in other situations up to 50% based on the number of moles of (A), (B) and (C). If the amount of anionic monomer (A) is too high, the polymer may not provide desired properties or may carry too much surfactant counter ion leading to an incompatible or non-flowable material. The amount of anionic monomer (A) can vary between any of the values recited above.

The monomer mixture can include cationic monomer (B) at a level of at least 1%, in some cases at least 5%, in other cases at least 10%, in some situations at least 15% and in other situations at least 20% based on the number of moles of (A), (B) and (C). When the amount of monomer (B) is too low, the resulting polymer can have poor compatibility and/or poor substantivity. Also, cationic monomer (B) can be present at up to 50%, in some cases up to 40%, in other cases up to 35%, in some situations up to 30% and in other situations up to 25% based on the number of moles of (A), (B) and (C). If the amount of cationic monomer (B) is too high, the polymer may not provide desired properties. The amount of cationic monomer (B) can vary between any of the values recited above.

The monomer mixture can optionally contain other monomers (C). When the monomers (C) are present, they are included at a level of at least 0.1%, in some cases at least 1%, in other cases at least 5% and in some situations at least 10% based on the number of moles of (A), (B) and (C). Also, when present, the other monomers (C) can be used at up to 80%, in some cases up to 70%, in other cases up to 60%, in some situations up to 50% and in other situations up to 40% based on the number of moles of (A), (B) and (C). The amount of other monomers (C) can vary between any of the values recited above.

The sum of the mole percentages of (A), (B) and (C) is typically 100%.

In an embodiment of the invention, the number of moles of acid functional monomer (A) is greater than the number of moles of cationic monomer (B). In this embodiment, the molar ratio of anionic monomer to cationic monomer can be at least 1.01:1, in some cases at least 1.05:1, in other cases at least 1.1:1 and in some situations at least 1.15:1. Also, the molar ratio of anionic monomer to cationic monomer can be up to 10:1, in some cases up to 5:1, in other cases up to 2.5:1, in some situations up to 2:1 and in certain instances up to 1.5:1. The molar ratio of anionic monomer to cationic monomer can be any of the values stated above or range between any of the values recited above.

In an embodiment of the invention, the anionic monomer (A) can include carboxylic acid functional monomers, sulfonic acid functional monomers and as well as combinations thereof. As a non-limiting example, the carboxylic acid functional monomers can include (meth)acrylic acid; maleic acid; itaconic acid; N-(meth)acrylamidopropyl, N,N-dimethyl, amino acetic acid; N-(meth)acryloyloxyethyl, N,N-dimethyl, amino acetic acid; N-(meth)acryloyloxypropyl, N,N-dimethyl, amino acetic acid; crotonic acid; (meth)acrylamidoglycolic acid; 2 (meth)acrylamido 2 methylbutanoic acid and mixtures thereof. Also, non-limiting examples of sulfonic acid functional monomers include 2-(meth)acrylamido-2-methylpropane sulfonic acid; sulfonated styrene; vinyl sulfonic acids; (meth)allyl ether sulfonic acids; (meth)allyloxy benzenesulfonic acid; and combinations thereof. In all cases, the corresponding salts of any of the acid functional monomers as well as any anhydrides can be used.

In a particular embodiment of the invention, the acid functional monomers are selected from (meth)acrylic acid and 2-(meth)acrylamido-2-methylpropane sulfonic acid. In an embodiment of the invention, the 2-(meth)acrylamido-2-methylpropane sulfonic acid monomer is included, along with a carboxylic acid functional monomer, in an amount sufficient to improve compatibility of the resulting polymer with other ingredients in a formulation in which the polymer is included. In this embodiment, the 2-(meth)acrylamido-2-methylpropane sulfonic acid can be included at a level of at least 1 mole %, in some cases at least 2 mole %, and in other cases at least 3 mole % and up to 20 mole %, in some cases up to 15 mole %, in other cases up to 10 mole % and in some situations up to 5 mole %. In this embodiment, the 2-(meth)acrylamido-2-methylpropane sulfonic acid monomer can be present at any level or can range between any level recited above.

In the present invention, the acid functional monomers are at least partially neutralized with a suitable amine as described above. Particular and non-limiting examples of suitable amines that can be used include oleamidopropyl dimethylamine, cocamidopropyl dimethylamine, stearamidopropyl dimethylamine, behenamidopropyl dimethylamine, soyamidopropyl dimethylamine, quaternary analogs of such amines as described in formulas (II) and (IV), and mixtures thereof.

In a particular embodiment of the invention, the amine is added to one or more carboxylic acid functional monomers to form a solution of the acid-amine salt and the remainder of the carboxylic acid monomer. The acid-amine mixture is then added to a mixture containing the remainder of the monomers, which are then polymerized as described below. By amine, in this context, is meant any compound according to formulas (I) through (IV) as described above. In this embodiment, the amount of amine can be an amount sufficient to provide at least 1%, in some cases at least 2%, in other cases at least 2.5%, in some situations at least 3% and in other situations at least 5% by weight of the combination of the monomers (A), (B), and (C) and amine. If the amount of amine is too low, the resulting polymer may not provide desired properties as indicated below. Also, the amount of amine can be an amount sufficient to provide up to 30%, in some cases up to 25% and in other cases up to 20% by weight of the combination of the monomers (A), (B), and (C) and amine. If the amount of amine is too high and depending on the particular amine, the resulting polymer may not provide suitably stable solutions/dispersions in water. The amount of amine in the present polymer can be any of the values recited above or can vary between any of the values recited above.

In a further embodiment of the invention, the degree of neutralization of the one or more carboxylic acid functional monomers provided by the amine can be at least 0.25%, in some cases at least 0.5%, in other cases at least 0.75%, and in some situations at least 1%. If the degree of neutralization provided by the amine is too low, the resulting polymer may not provide desired properties as indicated below. Also, the degree of neutralization provided by the amine can be up to 50%, in some cases up to 40%, in other cases up to 30%, in some situations up to 25%, in other situations up to 20% and in some instances up to 10%. If the amount of neutralization provided by the amine is too high and depending on the particular amine, the resulting polymer may not provide suitably stable solutions/dispersions in water. The degree of neutralization provided by the amine in the present polymer can be any of the values recited above or can vary between any of the values recited above.

A particular advantage in the present invention is that many polymer-cationic surfactant combinations that were not previously obtainable in a uniform desirable form can now be prepared in the form of a uniform stable complex. As a non-limiting example, amines which are either in a solid (lauramidopropyl dimethylamine as a non-limiting example), flake (stearamidodimethylamine or behenamidodimethylamine as non-limiting examples) or pastes (wheat germamidodimethylamine and soyamidodimethylamine as non-limiting examples) cannot be uniformly mixed with a polymer after polymerization. In the present invention, the above-mentioned types of surfactants can be dissolved by way of a neutralization reaction with the one or more carboxylic acid functional monomers, which are then added to an aqueous monomer phase and polymerized to form a stable polymer-surfactant complex as described below. In the cases of liquid amines, (cocamidodimethylamine and oleamido dimethylamine being non-limiting examples), mixing after polymerization typically leads to a non-uniform and undesirable paste. Using the present invention provides a uniform polymer surfactant complex.

In addition to the amines indicated above, other neutralizing agents known in the art can be used to neutralize the acid functional groups in the monomers in (A) either prior to or after polymerization. As such, aqueous solutions or mixtures containing the above-described complex can be neutralized to a pH to at least 2, in some cases at least 2.5, in other cases at least 3, in some situations at least 4 and in other situations at least 4.5. Also, the complexes can be neutralized to a pH of up to 9, in some cases up to 8.5, in other cases up to 8, in some situations up to 7.5, in other situations up to 7 and in certain instances up to 6.5. The present complexes can be neutralized to a pH ranging between any of the values recited above.

Any suitable cationic monomer can be used in (B). Non-limiting examples of suitable cationic monomers include (meth)acrylamidopropyltrimethyl ammonium halides, (meth)acryloyloxyethyltrimethyl ammonium halides, (meth)acryloyloxyethyltrimethyl ammonium methyl sulfate, diallyl dialkyl ammonium halides and in particular acrylamidopropyltrimethyl ammonium chloride (APTAC), methacrylamidopropyltrimethyl ammonium chloride (MAPTAC), diallyl dimethyl ammonium chloride (DADMAC), acryloyloxyethyl trimethyl ammonium chloride (AETAC), methacryloyloxyethyl trimethyl ammonium chloride (METAC) and mixtures thereof.

Any suitable monomer that is not included in (A) or (B) that will provide desired properties to the polymer can be used in the other monomers (C). Non-limiting examples of suitable other monomers (C) include (meth)acrylamide, $C_1$-$C_{22}$ linear or branched alkyl or aryl (meth)acrylate, $C_1$-$C_{22}$ linear or branched N-alkyl or N-aryl (meth)acrylamide, N-vinylpyrrolidone, vinyl acetate, $C_1$-$C_{22}$ linear or branched alkyl or aryl ethoxylated (meth)acrylate, $C_1$-$C_{22}$ linear or branched alkyl or aryl propoxylated (meth)acrylate; N,N—$C_1$-$C_{22}$ linear or branched dialkyl (meth)acrylamide, styrene, $C_1$-$C_{22}$ linear or branched alkyl or aryl allyl ethers and mixtures thereof.

In another embodiment of the invention, at least a portion of the anionic monomers in (A) used in the polymer-surfactant complex of the present invention include a surfactant, which is able to carry a cationic charge, as a counter ion. Any surfactant that is able to carry a cationic charge can be used. The amount of cationic charged surfactant used will depend on the amount of acid containing anionic monomer utilized in the present polymer-surfactant complex. The cationic charged monomer can be present at 0.1 to 100 mol %, in some cases from 1 to 90 mol %, in other cases from 5 to 80 mol % and certain situations from 10 to 75 mol % based on the amount of anionic monomer present in the polymer-surfactant complex of the present invention. The amount of surfactant, which is able to carry a cationic charge, can often depend on the degree of neutralization and/or the desired pH.

Any cationic surfactant can be used as a counter ion for the sulfonic acid containing anionic monomer of the present polymer-surfactant complex. Desirable cationic surfactants include, but are not limited to, quaternary ammonium surfactants represented by general formula (V):

$$N^+R^{10}_4 \qquad (V)$$

where each occurrence of $R^{10}$ is independently a $C_1$ to $C_{22}$ alkyl, aryl, alkyl aryl, $C_1$ to $C_{22}$ ethoxylated or propoxylated alkyl, ethoxylated or propoxylated aryl, or ethoxylated or propoxylated alkyl aryl group.

At appropriate pH ranges, amphoteric surfactants carry a cationic charge and can form suitable counter ion complexes with the anionic monomer of the present polymer-surfactant complex at the same levels as cationic surfactants. Without being construed as limiting the invention in any way, examples of surfactants which can be used in the present invention are those which are broadly described as derivatives of aliphatic secondary and tertiary amines in which the aliphatic substituent contains from about 8 to 18 carbon atoms and also contains an anionic water solubilizing group e.g., carboxy, sulfonate, sulfate, phosphate or phosphonate. Examples of compounds falling within this definition are sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products described in U.S. Pat. No. 2,528,378.

At appropriate pH ranges, zwitterionic surfactants carry a cationic charge and can form suitable counter ion complexes with the anionic monomer of the present polymer-surfactant complex at the same level as cationic surfactants. Examples of suitable zwitterionic surfactants include, but are not limited to betaines. Betaine surfactants that can be used in the present invention include the high alkyl betaines, such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, and lauryl bis-(2-hydroxypropyl)alpha-carboxyethyl betaine. The sulfobetaines can be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the RCONH($CH_2$)$_3$ radical is attached to the nitrogen atom of the betaine, are also useful in this invention.

The polymer-surfactant complexes of the present invention provide several advantages. The polymer-surfactant complexes provide a means of formulating with cationic charged surfactants in anionic surfactant formulations that would otherwise be incompatible with such surfactants. The polymer-surfactant complexes provide a means of delivering the cationic surfactants to the keratin substrate. Further, the combined action of the polymer and cationic charged surfactant provides enhanced and synergistic conditioning properties to hair, skin and nails not available in prior art formulations.

In an embodiment of the invention, the polymer in the polymer-surfactant complex of the invention can include a branching quantity of one or more monomers that have two or more sites of reactive unsaturation. In this embodiment, any suitable monomers that have two or more sites of reactive unsaturation can be used. Suitable monomers having two or more sites of reactive unsaturation include, but are not limited to, ethylene glycol di(meth)acrylate, triethylene glycol di(meth)acrylate, tetraethylene glycol di(meth)acrylate, 1,3-butylene glycol di(meth)acrylate, trimethylolpropane tri(meth)acrylate, 1,4-butanediol di(meth)acrylate, neopentyl glycol di(meth)acrylate, 1,6-hexanediol di(meth)acrylate, pentaerythritol di(meth)acrylate, pentaerythritol tri(meth)acrylate, pentaerythritol tetra(meth)acrylate, glycerol di(meth)acrylate, glycerol allyloxy di(meth)acrylate, 1,1,1-tris(hydroxymethyl)ethane di(meth)acrylate, 1,1,1-tris(hydroxymethyl)ethane tri(meth)acrylate, 1,1,1-tris(hydroxymethyl)propane di(meth)acrylate, 1,1,1-tris(hydroxymethyl)propane tri(meth)acrylate, triallyl cyanurate, triallyl isocyanurate, triallyl trimellitate, diallyl phthalate, diallyl terephthalate, divinyl benzene, triallylamine, methylenebis(meth)acrylamide, and combinations thereof.

The monomers having two or more sites of reactive unsaturation are present at 0.0001 to 1 mol %, in some cases 0.001 to 0.5 mol % and in other cases 0.01 to 0.25 mol % based on the total number of moles of (A), (B) and (C).

The weight average molecular weight of the polymer-surfactant complex is at least 1,000, in some cases at least 10,000, in other cases at least 25,000 and in some situations at least 50,000. Also, the weight average molecular weight of the polymer-surfactant complex can be up to 10,000,000, in some cases up to 8,000,000, in other cases up to 5,000,000, in some situations up to 1,000,000 and in other situations up to 500,0000. The weight average molecular weight can be determined by viscometry or by gel permeation chromatography (GPC) using appropriate standards; as a non-limiting example, sulfonated polystyrene standards can be used to determine molecular weight, in which case the Mw value is used as the molecular weight measurement. The Mw of the polymer-surfactant complex can be any of the values recited above and can vary between any of the values recited above.

When the molecular weight is determined by viscometry, the molecular weight can be estimated based on as a reduced viscosity value. The reduced viscosity is determined using a Ubbelohde Capillary Viscometer at 0.05% concentration of polymer in a 1M NaCl solution, pH 7, at 30° C. The reduced viscosity of the complex can be at least 0.1, in some cases at least 0.25, in other cases at least 0.5, in some situations at least 1 and in other cases at least 1.5 dl/g. Also, the reduced viscosity of the complex can be up to 30, in some cases up to 25, in other cases up to 20, in some situations up to 15 and in other cases up to 10 dl/g. The reduced viscosity of the polymer-surfactant complex can be any of the values recited above and can vary between any of the values recited above.

The present polymer-surfactant complexes can be prepared by conventional solution polymerization techniques, or alternatively by water-in-oil emulsion polymerization techniques. When preparing the present polymer-surfactant complex, the anionic monomer is at least partially neutralized as described above and the other monomers are appropriately combined therewith to form a monomer mixture. Thus, to prepare the instant polymers, the appropriate weights for the desired molar ratios of monomers are charged to a glass reactor equipped with a stirring means. The desired total monomer concentration is generally about 10-30% by weight. The monomer mixture is then adjusted to a desired pH as described above and heated, as a non-limiting example, to about 55° C., and purged with nitrogen for at least thirty minutes. Polymerization is then initiated by adding an effective amount of a free radical initiator, which as a non-limiting example can be $5 \times 10^{-2}$ mol % of sodium persulfate and $2.4 \times 10^{-3}$ mol % of sodium bisulfate. After polymerization is completed and a peak exotherm temperature is reached, additional dilution water and sodium bisulfite can be added to scavenge any residual monomer and to dilute the final product polymer solids.

The polymer of the present polymer-surfactant complex can be branched or crosslinked by including suitable "crosslinking" monomers in the polymerization process as described above.

Further, the polymer-surfactant complexes of the present invention can be purified or provided in a "narrow" molecular weight distribution form through art-recognized methods of polymer fractionation by using poor solvents and/or non-solvents for the polymer-surfactant complex. Other methods of fractionating the polymer-surfactant complex include, but are not limited to, precipitation and membrane separation, including the use of cross-flow membranes.

Embodiments of the present invention are also directed to compositions for treating a keratin-based substrate. The compositions contain an effective amount of the polymer-surfactant complexes, or an effective amount of a cosmetically acceptable medium containing the polymer-surfactant complexes. The cosmetically acceptable medium can contain at least 0.01%, in some cases at least 0.1%, in other cases at least 1%, in some situations at least 5%, and in other situations at least 10% by weight of the present polymer-surfactant complexes. Also, the cosmetically acceptable medium can contain up to 80%, in some cases up to 60%, in other cases up to 50%, in some situations up to 40%, in other situations up to 30% and in certain instances up to 20% by weight, based on the total weight of the cosmetically acceptable medium. The polymer-surfactant complexes of the present invention can be present in the cosmetically acceptable medium at any of the levels recited above and can vary between any of the values recited above.

The present compositions for treating keratin-based substrates can also include a suitable surfactant component. The surfactant component can include, but is not limited to amphoteric surfactants, cationic surfactants, nonionic surfactants, zwitterionic surfactants and combinations thereof. The surfactant component is in addition to the surfactants that are complexed with the anionic monomer as described above. The surfactant component, when present, can be included at a level of at least 1%, in some cases 5% and in other cases at least 10% by weight of the keratin-treating composition. Also, the surfactant component can be present at up to 50%, in some cases up to 35% and in other cases up to 20% by weight of the keratin-treating composition. The surfactant component can be present in the keratin-treating composition at any level recited above or range between any amounts recited above.

Non-limiting examples of amphoteric surfactants, cationic surfactants, and zwitterionic surfactants that can be used in the surfactant component are those identified above.

Nonionic surfactants which can be used in the surfactant component of the keratin-treating composition include those broadly defined as compounds produced by the condensation of alkylene oxide groups (hydrophilic in nature) with an organic hydrophobic compound, which can be aliphatic or alkyl aromatic in nature. Non-limiting examples of classes of nonionic detersive surfactants are the long chain alkanolamides; the polyethylene oxide condensates of alkyl phenols; the condensation product of aliphatic alcohols having from about 8 to about 18 carbon atoms, in either straight chain or branched chain configuration, with ethylene oxide; the long chain tertiary amine oxides; the long chain tertiary phosphine oxides; the long chain dialkyl sulfoxides containing one short chain alkyl or hydroxy alkyl radical of from about 1 to about 3 carbon atoms; the alkyl polysaccharide (APS) surfactants such as the alkyl polyglycosides; and the polyethylene glycol (PEG) glyceryl fatty esters.

In an embodiment of the invention, the cosmetic acceptable medium can be selected, inter alia, from a conditioner, a hair dye, a permanent wave, a hair relaxer, a hair bleach, a hair setting composition, a styling gel, a mousse, a hair gel, an aftershave, a sunscreen, a hand lotion, a moisturizer, and a shaving cream.

The keratin-treating composition and/or cosmetically acceptable medium can be in the form of a liquid, cream, emulsion, gel, thickening lotion or powder. Further, the keratin-treating composition and/or cosmetically acceptable medium can contain water and also any cosmetically acceptable solvents, in particular monoalcohols, such as alkanols having 1 to 8 carbon atoms (like ethanol, isopropanol, benzyl alcohol and phenylethyl alcohol); polyalcohols, such as alkylene glycols (like glycerine, ethylene glycol and propylene glycol); and glycol ethers, such as mono-, di- and tri-ethylene glycol monoalkyl ethers (like ethylene glycol monomethyl ether and diethylene glycol monomethyl ether), used singly or in a mixture. These solvents can be present in proportions of up to as much as 70% by weight, relative to the weight of the total composition.

Useful compositions according to the invention can also contain electrolytes, such as aluminum chlorohydrate, alkali metal salts, e.g., sodium, potassium or lithium salts, these salts can be halides, such as the chloride or bromide, and the sulphate, or salts with organic acids, such as the acetates or lactates, and also alkaline earth metal salts. In many cases the carbonates, silicates, nitrates, acetates, gluconates, pantothenates and lactates of calcium, magnesium and strontium are used.

These compositions can also be presented in the form of a powder or of lyophilisates to be diluted before use.

The compositions according to the present invention can contain any other ingredient normally used in cosmetics, such as perfumes, dyestuffs which can serve to color the composition itself or hair fibers, preservatives, sequestering agents, thickeners, silicones, softeners, foam synergistic agents, foam stabilizers, sun filters, peptising agents and also anionic, nonionic, cationic or amphoteric surface-active agents or mixtures thereof.

These compositions can be used, in particular, in the form of a cream, a gel, or a treatment product which can be applied before or after coloring or bleaching, before or after shampooing, before or after perming or before or after straightening, and can also adopt the form of a coloring product, a setting lotion, a brushing lotion, a bleaching product, a perming product or a straightening product.

The keratin-treating compositions of the present invention optionally contain a nonvolatile, water insoluble, organic, oily liquid as a conditioning agent. The conditioning oily liquid can protect, lubricate and/or moisturize the skin and add shine, softness and luster to the hair. Additionally, it can also enhance dry combing and dry hair feel. The hair conditioning oily liquid is typically present in the compositions at a level of from about 0.05% to about 5% by weight of the composition, in some cases from about 0.2% to about 3% and in other cases from about 0.5% to about 1%.

By "nonvolatile" what is meant is that the oily material exhibits very low or no significant vapor pressure at ambient conditions (e.g., 1 atmosphere, 25° C.), as is understood in the art. The nonvolatile oily materials desirably have a boiling point at ambient pressure of about 250° C. or higher.

By "water insoluble" what is meant is that the oily liquid is not soluble in water (distilled or equivalent) at a concentration of 0.1% at 25° C.

The conditioning oily liquids hereof generally will have a viscosity of about 3 million centistokes (cs) or less, in some cases about 2 million cs or less and in other cases about 1.5 million cs or less.

The conditioning oily materials hereof are liquids selected from hydrocarbon oils and fatty esters. The fatty esters hereof are characterized by having at least 12 carbon atoms, and include esters with hydrocarbon chains derived from fatty acids or alcohols, e.g., mono-esters, polyhydric alcohol esters, and di- and tri-carboxylic acid esters. The hydrocarbyl radicals of the fatty esters hereof can also include or have covalently bonded thereto other compatible functionalities, such as amides and alkoxy moieties (e.g., ethoxy or ether linkages, etc.).

Hydrocarbon oils include cyclic hydrocarbons, straight chain aliphatic hydrocarbons (saturated or unsaturated), and branched-chain aliphatic hydrocarbons (saturated or unsaturated). Straight chain hydrocarbon oils useful in the invention can contain from about 12 to about 19 carbon atoms, although it is not necessarily meant to limit the hydrocarbons to this range. Branched chain hydrocarbon oils can and typically can contain higher numbers of carbon atoms. Also encompassed herein are polymeric hydrocarbons of alkenyl monomers, such as $C_2$-$C_6$ alkenyl monomers. These polymers can be straight or branched-chain polymers. The straight chain polymers will typically be relatively short in length, having a total number of carbon atoms as described above for straight chain hydrocarbons in general. The branched-chain polymers can have substantially higher chain length. The number average molecular weight of such materials can vary widely, but will typically be up to about 500, in some cases from about 200 to about 400, and in other cases from about 300 to about 350.

Specific examples of suitable materials include, but are not limited to, paraffin oil, mineral oil, saturated and unsaturated dodecane, saturated and unsaturated tridecane, saturated and unsaturated tetradecane, saturated and unsaturated pentadecane, saturated and unsaturated hexadecane, and mixtures thereof. Branched-chain isomers of these compounds, as well as of higher chain length hydrocarbons, can also be used. Exemplary branched-chain isomers are highly branched saturated or unsaturated alkanes such as the permethyl-substituted isomers, e.g., the permethyl-substituted isomers of hexadecane and undecane, such as 2,2,4,4,6,6,8,8-dimethyl-10-methylundecane and 2,2,4,4,6,6-dimethyl-8-methyl-nonane, sold by Permethyl Corporation. A non-limiting example of a hydrocarbon polymer is polybutene, such as the copolymer of isobutylene and butene. A commercially available material of this type is L-19 polybutene from Amoco Chemical Co. (Chicago, Ill., USA)

Monocarboxylic acid esters hereof include esters of alcohols and/or acids of the formula R'COOR, wherein R' and R are alkyl or alkenyl radicals and the sum of carbon atoms in R' and R is at least 10, in many cases at least 20.

Fatty esters include, for example, alkyl and alkenyl esters of fatty acids having aliphatic chains with from about 10 to about 22 carbon atoms, and alkyl and alkenyl fatty alcohol carboxylic acid esters having an alkyl and/or alkenyl alcohol-derived aliphatic chain with about 10 to about 22 carbon atoms, and combinations thereof. Examples include isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyl decyl adipate, lauryl lactate, myristyl lactate, cetyl lactate, oleyl stearate, oleyl oleate, oleyl myristate, lauryl acetate, cetyl propionate and oleyl adipate.

The mono-carboxylic acid ester, however, need not necessarily contain at least one chain with at least 10 carbon atoms, so long as the total number of aliphatic chain carbon atoms is at least 10. Examples include diisopropyl adipate, diisohexyl adipate and diisopropyl sebacate.

Di- and tri-alkyl and alkenyl esters of carboxylic acids can also be used. These include, for example, esters of $C_4$-$C_8$ dicarboxylic acids such as $C_1$-$C_{22}$ esters (in many cases $C_1$-$C_6$) of succinic acid, glutaric acid, adipic acid, hexanoic acid, heptanoic acid and octanoic acid. Specific examples include isocetyl stearyl stearate, diisopropyl adipate and tristearyl citrate. Polyhydric alcohol esters include alkylene glycol mono and di-fatty acid esters, propylene glycol mono- and di-fatty acid esters, polypropylene glycol mono oleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters and polyoxyethylene sorbitan fatty acid esters are satisfactory polyhydric alcohol esters for use herein.

Glycerides include mono-, di- and tri-glycerides. More specifically, included are the mono-, di- and tri-esters of glycerol and long chain carboxylic acids, such as $C_{10}$-$C_{22}$ carboxylic acids. A variety of these types of materials can be obtained from vegetable and animal fats and oils, such as castor oil, safflower oil, cotton seed oil, corn oil, olive oil, cod liver oil, almond oil, avocado oil, palm oil, sesame oil, lanolin and soybean. Synthetic oils include triolein and tristearin glyceryl dilaurate. In an embodiment of the invention, the glycerides are di- and tri-glycerides and in a particular embodiment triglycerides are used.

The keratin-treating compositions of the present invention optionally contain a nonvolatile, nonionic silicone conditioning agent which is insoluble in the compositions hereof. The silicone conditioning agent is intermixed in the composition so as to be in the form of dispersed, insoluble particles or droplets. The silicone conditioning agent comprises a nonvolatile, insoluble, silicone fluid and optionally comprises a silicone gum which is insoluble in the composition as a whole, but is soluble in the silicone fluid. The silicone conditioning agent can also comprise other ingredients, such as a silicone resin, to enhance deposition efficiency.

The silicone conditioning agent can include low levels of volatile silicone components; however, such volatile silicones in many cases exceed no more than about 0.5%, by weight, of the composition. Typically, if volatile silicones are present, it will be incidental to their use as a solvent or carrier for commercially available forms of other ingredients, such as silicone gums and resins.

The silicone conditioning agent for use herein can have a viscosity of from about 1,000 to about 2,000,000 centistokes (cs) at 25° C. using a glass capillary viscometer, in some cases from about 10,000 to about 1,800,000 cs, and in other cases from about 100,000 to about 1,500,000 cs.

The silicone conditioning agent will be used in the compositions hereof at levels of from about 0.5% to about 10% by weight of the composition, in some cases from about 0.1% to about 10%, in other cases from about 0.5% to about 8%, and in some instances from about 0.5% to about 5%. The silicone conditioning agent can also be used in combination with the organic water insoluble liquid.

Suitable insoluble, nonvolatile silicone fluids include, but are not limited to, polyalkyl siloxanes, polyaryl siloxanes, polyalkylaryl siloxanes, polyether siloxane copolymers, and mixtures thereof. Other insoluble, nonvolatile silicone fluids having conditioning properties can also be used. The term "nonvolatile" as used herein shall mean that the silicone material exhibits very low or no significant vapor pressure at ambient conditions, as is understood by those in the art. The term "silicone fluid" shall mean flowable silicone materials having a viscosity of less than 1,000,000 cs at 25° C. Generally, the viscosity of the fluid will be between about 5 and 1,000,000 cs at 25° C., in some cases between about 10 and about 100,000 cs.

The nonvolatile polyalkylsiloxane fluids that can be used include, for example, polydimethyl siloxanes. These siloxanes are available, for example, from the General Electric Company in their Viscasil® and SF96® series, and from Dow Corning in their Dow Corning 200® series.

The polyalkylaryl siloxane fluids that can be used, also include, for example, polymethylphenylsiloxanes. These siloxanes are available, for example, from the General Electric Company as SF 1075 methyl phenyl fluid or from Dow Corning as 556 Cosmetic Grade Fluid.

The polyether siloxane copolymers that can be used include, for example, a polypropylene oxide modified polydimethylsiloxane (e.g., Dow Corning DC-1248), although ethylene oxide or mixtures of ethylene oxide and propylene oxide can also be used. The ethylene oxide and polypropylene oxide level must be sufficiently low to prevent solubility in water and the composition hereof.

References disclosing suitable silicone fluids include U.S. Pat. No. 2,826,551 to Geen; U.S. Pat. No. 3,964,500 to Drakoff; U.S. Pat. No. 4,364,837 to Pader; U.S. Pat. No. 5,573,709 to Wells; British Patent 849,433 to Woolston; and PCT Patent Application WO93/08787, the pertinent portions of which are incorporated herein by reference in their entireties.

Another silicone material that can be especially useful in the silicone conditioning agents is insoluble silicone gum. The term "silicone gum," as used herein, means polyorganosiloxane materials having a viscosity at 25° C. of greater than or equal to 1,000,000 cs. Silicone gums are described, for example, in U.S. Pat. No. 4,152,416 to Spitzer et al. The "silicone gums" will typically have a mass molecular weight in excess of about 200,000, generally between about 200,000 and about 1,000,000. Specific examples include polydimethylsiloxane, (polydimethyl siloxane) (methylvinylsiloxane) copolymer, poly(dimethyl siloxane) (diphenyl siloxane) (methylvinylsiloxane) copolymer and mixtures thereof.

The silicone conditioning agent can include a mixture of a polydimethylsiloxane gum having a viscosity greater than about 1,000,000 cs and polydimethyl siloxane fluid having a viscosity of from about 10 cs to about 100,000 cs, wherein the ratio of gum to fluid is from about 30:70 to about 70:30, in some cases from about 40:60 to about 60:40.

Another optional ingredient that can be included in the silicone conditioning agent is silicone resin. Silicone resins are highly crosslinked polymeric siloxane systems. The crosslinking is introduced through the incorporation of trifunctional and tetrafunctional silanes with monofunctional or difunctional, or both, silanes during manufacture of the silicone resin. As is well understood in the art, the degree of crosslinking that is required in order to result in a silicone resin will vary according to the specific silane units incorporated into the silicone resin.

In general, silicone materials which have a sufficient level of trifunctional and tetrafunctional siloxane monomer units (and hence, a sufficient level of crosslinking) such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. In many cases, the ratio of oxygen to silicon atoms is at least about 1.2:1.0. Silanes used in the manufacture of silicone resins include monomethyl-, dimethyl-, trimethyl-, monophenyl-, diphenyl-, methylphenyl-, monovinyl-, and methylvinyl-chlorosilanes, and tetrachlorosilane, with the methyl-substituted silanes being most commonly utilized. Non-limiting examples of resins that can be used are those offered by General Electric as GE SS4230 and SS4267. Commercially available silicones resins will generally be supplied in a dissolved form in a low viscosity volatile or nonvolatile silicone fluid. The silicone resins for use herein should be supplied and incorporated into the present compositions in such dissolved form, as will be readily apparent to those skilled in the art.

Examples of desirable optional silicones useful in the invention include dimethicone, cyclomethicone, trimethyl silyl amodimethicone, phenyl trimethicone, trimethyl siloxy silicate, polyorganosiloxane, polyalkylsiloxane, polyarylsiloxane, polyalkylarylsiloxane and polyestersiloxane copolymers.

The keratin-treating compositions of the present invention are typically liquids which, desirably, are pourable at room temperature. The compositions hereof will comprise an aqueous carrier, i.e., water, which will generally be present at a level of about 20% to about 95% by weight of the composition, in many cases from about 60% to about 85% for pourable, liquid formulations such as shampoos, shower gels, liquid handsoaps, and lotions. The compositions of the present invention can also be in other forms, such as gels, mousse, etc. In such cases, appropriate components known in the art, such as gelling agents (e.g., hydroxyethyl cellulose), etc., can be included in the compositions. Gels will typically contain from about 20% to about 90% water. Mousses will be a low viscosity composition and will be packaged as a sprayable liquid according to techniques well known in the art, typically in an aerosol canister including a propellant or a means for generating an aerosol spray.

The present keratin-treating compositions can also comprise a variety non-essential, optional components suitable for rendering such compositions more cosmetically or aesthetically acceptable or to provide them with additional usage benefits. A variety of such are known to those skilled in the art in hair, skin and nail care. These ingredients are well-known and include, without limiting the invention thereto, pearlescent aids, such as coated mica, ethylene glycol distearate; opacifiers, such as tin; preservatives, such as 1,2-dibromo-2,4-dicyano butane (MERGUARD® Nalco Chemical Company, Naperville, Ill., USA), benzyl alcohol, 1,3-bis(hydroxymethyl)-5,5-dimethyl-2,3-imidazolidinedione (e.g., GLYDANT®, Lonza Inc., Fairlawn, N.J., USA), methylchloroisothiazolinone (e.g., KATHON®, Rohm & Haas Co., Philadelphia, Pa., USA), methyl paraben, propyl paraben, and imidazolidinyl urea; fatty alcohols, such as cetearyl alcohol, cetyl alcohol, and stearyl alcohol; sodium chloride; ammonium chloride; sodium sulfate; ethyl alcohol; pH adjusting aids, such as citric acid, sodium citrate, succinic acid, phosphoric acid, monosodium phosphate, disodium phosphate, sodium hydroxide, and sodium carbonate; coloring agents or dyes; perfumes; and sequestering agents, such as disodium ethylenediamine tetra-acetate (EDTA).

Another optional ingredient that can be advantageously used is an anti-static agent. The anti-static agent should not unduly interfere with the in-use performance and end-benefits of the composition. This is more important for shampoo compositions, and the anti-static agent should particularly not interfere with the anionic detersive surfactant. Suitable anti-static agents include, for example, tricetyl methyl ammonium chloride.

Typically, from about 0.1% to about 5% of such anti-static agent is incorporated into the shampoo compositions.

Though the polymer components can act to thicken the present compositions to some degree, the present compositions can also optionally contain other thickeners and viscosity modifiers such as an ethanolamide of a long chain fatty acid, such as polyethylene (3) glycol lauramide and coconut monoethanolamide (cocamide MEA), ammonium xylene sulfonate, xanthan gum and hydroxyethyl cellulose.

The optional components can be included in the compositions of the present invention at a level of from about 0.01% to about 10%, and in some cases from about 0.05% to about 5.0%, of the composition.

Further, the instant invention is directed to a method for treating a keratin-containing substrate that includes contacting the substrate with the above defined polymer-surfactant complexes, cosmetically acceptable medium, and/or keratin-treating compositions. The keratin-containing substrate can be human hair, human skin and/or human nails.

In an embodiment of the method of treating keratin-based substrates, the substrates can be contacted with a cosmetically acceptable medium containing from 0.1-99.9% by weight of the polymer surfactant complex.

The compositions of the present invention are utilized conventionally, i.e., the hair or skin is conditioned by applying an effective amount of the composition to the scalp or skin, and optionally rinsing with water. The term an "effective amount" as used herein, is an amount which is effective in conditioning, i.e., moisturizing hair and/or skin, making hair easier to comb, revitalizing hair, or removing or minimizing wrinkles in skin. Generally, from about 1 g to about 20 g of the composition is applied for conditioning the keratin substrate.

On hair, the compositions can be left on the hair "as is" or the hair can be rinsed with water after application.

The compositions hereof can also be useful for conditioning the skin. For such applications, the composition would be applied to the skin in a conventional manner, such as by rubbing or massaging the skin with the composition, optionally in the presence of water, and then rinsing with water. In the case of non-rinse-off products, the composition is left in full concentration in contact with the skin.

If the compositions are presented in the form of a thickened lotion or a gel, they contain thickeners in the presence or absence of a solvent. The thickeners which can be used are especially carbopol, xanthan gums, sodium alginates, gum arabic and cellulose derivatives, and it is also possible to achieve thickening by means of a mixture of polyethylene glycol stearate or distearate or by means of a mixture of a phosphoric acid ester and an amide. The concentration of thickener is generally 0.05 to 15% by weight. If the compositions are presented in the form of a styling lotion, shaping lotion or setting lotion, they generally comprise, in aqueous, alcoholic or aqueous-alcoholic solution, the polymer-surfactant complexes defined above.

If the compositions of the instant invention are intended for use in the dyeing of keratin fibers, and in particular human hair, they generally contain at least one oxidation dyestuff precursor and/or one direct dyestuff in addition to the present polymer-surfactant complexes. They can also contain any other adjuvant normally used in this type of composition.

The pH of the dyeing compositions is generally 7 to 11 and can be adjusted to the desired value by adding an alkalizing agent.

The compositions according to the present invention can also be used for waving or straightening the hair. In this case, the composition generally contains, in addition to the instant polymer-surfactant complexes, one or more reducing agents and, if appropriate, other adjuvants normally used in this type of composition; such compositions are intended for use conjointly with a neutralizing composition.

The present invention will further be described by reference to the following examples. The following examples are merely illustrative of the invention and are not intended to be limiting. Unless otherwise indicated, all percentages are by weight.

Example 1

A monomer mix containing 46.9 gm of acrylamide (AM), 38 gm of acrylic acid (AA), 10.3 gm of the sodium salt of 2-acrylamido-2-methylpropane sulfonic acid (NaAMPS), 102 gm of acryloyloxyethyl trimethyl ammonium chloride (AETAC), 38 gm of soyamidopropyl dimethylamine (CHEMDEX® SO, Lubrizol Corporation), 13.4 gm of sodium hydroxide, 0.13 gm of the tetrasodium salt of ethylenediamine tetracetic acid (EDTA), and 1052.1 gm of de-ionized water was prepared. The solution was heated to 65° C. and purged with nitrogen for 30 minutes. Solutions of 0.3 gm of sodium persulfate in 3 gm of de-ionized water and 0.063 gm of sodium metabisulfite in 3.8 gm of de-ionized water were added to initiate the polymerization. After 45 minutes, 5 gm of sodium metabisulfite and 392.5 gm of de-ionized water were added. The resulting sample was a complex of soyamido propyl dimethylamine with a tetrapolymer of AM, AA, AMPS and AETAC having a relative monomer mole ratio of 37.5/30/2.5/30. The sample contained 11.5% active polymer and had a Brookfield viscosity of 26,600 cps. as measured by a RV model at 20 rpm with a spindle #6 at 25° C. The weight ratio of polymer to fattyamido tertiary amine was 84:16.

Example 2

A similar polymer complex was prepared as described in Example 1, except cocamidopropyl diamethylamine (CHEMDEX® C, Lubrizol Corporation) was used in place of the soyamidopropyl dimethylamine. The resulting sample was a complex of cocamidopropyl dimethylamine with a tetra polymer of AM/AA/AMPS/AETAC having a relative molar monomer ratio of 37.5/30/2.5/30. The sample had a Brookfield viscosity of 29,200 cps. as measured by a RV model at 20 rpm with a spindle #6 at 25° C. The weight ratio of polymer to fattyamido tertiary amine was 84:16.

Example 3

A complex of stearamidopropyl dimethylamine (CHEMDEX® S, Lubrizol Corporation) with a tetrapolymer of AM/AA/AMPS/AETAC having a relative molar ratio of 37.5/30/2.5/30 was prepared as described in Example 1, except that only 19 gm of stearamidopropyl dimethylamine was added and dissolved into the acrylic acid. The sample had a Brookfield viscosity of 9,900 cps, measured as described above.

Example 4

Comparative to Example 1

A tetrapolymer of AM, AA, AMPS and AETAC with the monomer mole ratio of Example 1 was prepared without the addition of the fatty amido dimethylamine. The sample contained 11.5% active polymer and had Brookfield viscosity of 5,000 cps as measured above.

Example 5-12

A series of tetrapolymers and terpolymers complexed with various fatyamido tertiary amines were prepared as described in Example 1 are described in the table below.

|  | Polymer Composition (mole ratio) | | | | | Polymer/ Amine Weight |
|---|---|---|---|---|---|---|
| Example | AM | AA | AMPS | AETAC | Fatty Amines* | Ratio |
| 1 | 37.5 | 30 | 2.5 | 30 | Soyamido- | 84/16 |
| 2 | 37.5 | 30 | 2.5 | 30 | Cocamido- | 84/16 |
| 3 | 37.5 | 30 | 2.5 | 30 | Stearamido- | 91/9 |
| 4** | 37.5 | 30 | 2.5 | 30 | — | 100/0 |
| 5 | 20 | 25 | 10 | 45 | Cocamido- | 80/20 |
| 6 | 20 | 25 | 10 | 45 | Stearamido- | 96/4 |
| 7** | 20 | 25 | 10 | 45 | — | 100/0 |
| 8 | 40 | 40 | — | 20 | Cocamido- | 87/13 |
| 9 | 40 | 40 | — | 20 | Soyamido- | 87/13 |
| 10 | 40 | 40 | — | 20 | Stearamido- | 90/10 |
| 11 | 40 | 40 | — | 20 | Behenamido- | 96/4 |
| 12** | 40 | 40 | — | 20 | — | 100/0 |

*Fatty amine: fatty amidopropyl dimethylamine
**Example 4, 7, 12 are comparative examples.

Example 13

A terpolymer of acrylamide (AM), acrylic acid (AA) and methacrylamidopropyl trimethylammonium chloride (MAPTAC) with a relative monomer molar ratio of 40/40/20 was prepared with stearalmidopropyl dimethylamine as described in Example 1. The polymer/amine weight ratio was 88/12.

Example 14

A terpolymer of vinylpyrrolidone (VP), acrylic acid (AA) and methacrylamidopropyl trimethylammonium chloride (MAPTAC) with a relative monomer mole ratio of 34.7/41.8/23.5 was prepared with stearamidopropyl dimethylamine as described in Example 1. The polymer amine weight ratio was 89/11.

Example 15

A copolymer of acrylic acid (AA) and diallyldimethyl ammonium chloride (DADMAC) with a relative mole ratio 36/64 was prepared with stearamidopropyl dimethylamine as described in Example 1. The polymer/amine weight ratio was 84/14.

Example 16

This example demonstrates the use of some of the compositions in the previous examples in a shampoo formulation. A viscous shampoo base was prepared using the ingredients in the table below (control formulation).

| Ingredients | % w/w |
|---|---|
| Water, de-ionized | add to 100 |
| Ammonium Laureth-3 sulfate | 6.0 |
| Ammonium Lauryl Sulfate | 4.0 |
| Cocamidopropyl Betaine | 4.0 |
| Coconut Monoethanolamide | 1.0 |
| Citric Acid | q.s. |
| Sodium Chloride | q.s. |
| Tetrasodium EDTA | 0.2 |

The shampoo as described above was evaluated by applying the formulation as described to the scalp and also formulations where 0.5 wt. % of the indicated compositions were added to the shampoo formulation and evaluated. A panel of eight adults evaluated the shampoo formulations according to their overall feel. The evaluations used the following scale:

5=Significant Improvement
4=Some Improvement over Control
3=No different than Control
2=Slightly Worse than Control
1=Much worse than Control The average results from the evaluation panel are shown in the table below.

| Example | Overall Rating |
|---|---|
| Control | 3.0 |
| 1 | 3.8 |
| 2 | 3.8 |
| 3 | 4.0 |
| 4* | 3.2 |
| 10 | 4.2 |
| 12* | 2.8 |
| 14 | 3.4 |

*Example 4 and 12 are comparative examples.

The examples demonstrate the improved hair properties observed when the polymer-surfactant complexes according to the invention are used as conditioning additives in a conditioning shampoo formulation.

Example 17

This example demonstrates the use of some of the compositions in the previous examples in an after shampoo conditioner formulation. A 2% active polymer solution was prepared by diluting the polymer/amine compositions with de-ionized water. The 2% solution was applied separately as an after shampoo conditioner. The base shampoo described above without using an after shampoo conditioner was used as a control. A panel of eight adults evaluated the conditions. The average panel test result are summarized in the following table.

| Example | Overall Rating |
|---|---|
| Control | 3.0 |
| 1 | 4.2 |
| 2 | 4.0 |
| 3 | 4.4 |
| 4* | 3.8 |
| 5 | 4.0 |
| 10 | 4.4 |
| 12* | 3.4 |

*Example 4 and 12 are comparative examples.

The examples demonstrate the improved hair properties observed when the polymer-surfactant complexes according to the invention are used as an after shampoo conditioner.

Example 18

This example demonstrates the use of the composition according to Example 10 in a body wash formulation. An oil free body wash was prepared using the ingredients in the table below.

| Ingredients | % w/w |
|---|---|
| Water, de-ionized | add to 100 |
| Sodium Laureth-2 Sulfate | 6.0 |
| Disoium Laureth Sulfosuccinate | 4.0 |
| Cocamide MEA | 1.0 |
| Cocamidopropyl Betaine | 2.0 |
| Glycol Stearate | 1.0 |
| Example 10 | 4.0 |
| Glycerin | 0.2 |
| Citric Acid | q.s. |
| Sodium Chloride | q.s. |
| Tetrasodium EDTA | 0.2 |

The formulation provided excellent skin feel properties. The Example demonstrates the desirable use of the present polymer/fatty amine complexes in a body wash formulation.

Example 19

This example demonstrates the use of the composition according to Example 10 in a moisturizing cream formulation. A rich moisturizing cream using the polymer/fatty amine complex of Example 10 was prepared using the ingredients in the table below.

|   | Ingredients | % w/w |
|---|---|---|
| A | Ceteareth-6/Cetearyl Alcohol | 2.0 |
|   | Ceteareth-25 Alcohol | 2.0 |
|   | Cetearyl Alcohol | 1.5 |
|   | Isopropyl Myristate | 4.0 |
|   | Octyl Palmitate | 3.0 |
|   | Glyceryl Stearate | 3.0 |
|   | Anhydrous Lanolin | 2.0 |
|   | Dimethicone, 350 cps. | 1.0 |
| B | Example 10 | 5.0 |
|   | 1,2 Propylene Glycol | 3.0 |
|   | Water, de-ionized | 74.5 |

Components A and B were combined to provide a moisturizing cream.

The present invention has been described with reference to specific details of particular embodiments thereof. It is not intended that such details be regarded as limitations upon the scope of the invention.

We claim:

1. A method of treating a keratin-based substrate comprising applying to said keratin-based substrate a cosmetically acceptable medium containing from 0.1-99.9% by weight of a polymer surfactant complex;
wherein the polymer surfactant is formed by polymerizing a monomer mixture comprising:
(A) acid functional monomers at least partially neutralized with one or more amines according to one or more of formulas (I) through (IV):

  (I)

  (II)

  (III)

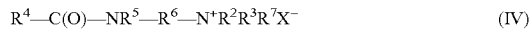  (IV)

wherein $R^1$ and $R^4$ are independently $C_8$-$C_{24}$ linear, branched or cyclic alkyl, aryl, alkenyl, aralkyl or aralkyl; $R^2$, $R^3$ and $R^5$ are independently H or $C_1$-$C_6$ linear, branched or cyclic alkyl, or where $R^2$ and $R^3$ combine to form an anelled ring of from 4 to 12 carbon atoms in length optionally containing hetero atoms along the ring selected from O, S, or N; $R^6$ is $C_1$-$C_{24}$ linear, branched or cyclic alkylene, arylene, alkenylene, aralkylene or aralkylene, $R^7$ is H, $C_1$-$C_{12}$ linear, branched or cyclic alkylene, arylene, alkenylene, aralkylene or aralkylene, and X is a halide, a sulfate or a sulfonate;
(B) one or more cationic monomers; and optionally
(C) one or more other monomers.

2. The method according to claim 1, wherein the acid functional monomers are (meth)acrylic acid and 2-(meth)acrylamido-2-methylpropane sulfonic acid.

3. The method according to claim 1, wherein the cationic monomers are selected from the group consisting of (meth)acrylamidopropyltrimethyl ammonium halides, (meth)acryloyloxyethyltrimethyl ammonium halides, (meth)acryloyloxyethyltrimethyl ammonium methyl sulfate, diallyl dialkyl ammonium halides, and mixtures thereof.

4. The method according to claim 1, wherein the amines are selected from oleamidopropyl dimethylamine, cocamidopropyl dimethylamine, stearamidopropyl dimethylamine, behenamidopropyl dimethylamine, soyamidopropyl dimethylamine, and mixtures thereof.

5. The method according to claim 1, wherein the other monomers are selected from the group consisting of (meth)acrylamide, $C_1$-$C_{22}$ linear or branched alkyl or aryl (meth)acrylate, $C_1$-$C_{22}$ linear or branched N-alkyl or N-aryl (meth)acrylamide, N-vinylpyrrolidone, vinyl acetate, $C_1$-$C_{22}$ linear or branched alkyl or aryl ethoxylated (meth)acrylated, $C_1$-$C_{22}$ linear or branched alkyl or aryl propoxylated (meth)acrylate; N,N—$C_1$-$C_{22}$ linear or branched dialkyl (meth)acrylamide, styrene, $C_1$-$C_{22}$ linear or branched alkyl or aryl allyl ethers, and mixtures thereof.

6. The method according to claim 1, wherein the weight average molecular weight of the polymer is at least 1,000 as determined using gel permeation chromatography using sulfonated polystyrene standards.

7. The method according to claim 1, wherein the polymer has a reduced viscosity determined using a Ubbelohde Capillary Viscometer at 0.05% concentration of polymer in a 1M NaCl solution, pH 7, at 30° C. of from 0.1 to 30 dl/g.

8. The method according to claim 1, wherein the number of moles of acid functional monomer (A) is greater than the number of moles of cationic monomer (B).

9. The method according to claim 1, wherein the anionic monomer (A) is present at from 20% to 90%, the cationic monomer (B) is present at from 5% to 50%, and the other monomer (C) is present at from 0.1% to 80% based on the number of moles of (A), (B) and (C), wherein the sum percentage of the moles of (A), (B) and (C) is 100%.

10. The method according to claim 1, wherein the cosmetically acceptable medium comprises from 5% to 50%, by weight, of a surfactant component selected from the group consisting of amphoteric surfactants, cationic surfactants, nonionic surfactants, and zwitterionic surfactants.

11. The method according to claim 10, wherein the amphoteric surfactant is one or more selected from the group consisting of sodium 3-dodecyl-aminopropionate, sodium 3-dodecylaminopropane sulfonate, sodium lauryl sarcosinate and N-alkyltaurines.

12. The method according to claim 10, wherein the zwitterionic surfactant is one or more selected from the group consisting of coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, coco dimethyl sulfopropyl betaine, stearyl dimethyl sulfopropyl betaine, lauryl dimethyl sulfoethyl betaine, lauryl bis-(2-hydroxyethyl) sulfopropyl betaine, amidobetaines, and amidosulfobetaines.

13. The method according to claim 1, wherein the cosmetically acceptable medium comprises a silicone conditioning agent.

14. The method according to claim 1, wherein the cosmetically acceptable medium comprises an organic water insoluble liquid selected from the group consisting of hydrocarbon oils, fatty esters having 10 to 22 carbon atoms, and mixtures thereof.

15. The method according to claim 1, wherein the cosmetically acceptable medium is selected from the group consisting of a conditioner, a hair dye, a permanent wave, a hair relaxer, a hair bleach, a hair setting composition, a styling gel, a mousse, a hair gel, an aftershave, a sunscreen, a hand lotion, a moisturizer and a shaving cream.

16. The method according to claim 1, wherein the keratin-based substrate is selected from human hair, human skin and human nails.

17. The method according to claim 1, wherein the cosmetically acceptable medium comprises one or more other conditioning additives.

\* \* \* \* \*